United States Patent
Vornlocher et al.

(10) Patent No.: US 10,501,740 B2
(45) Date of Patent: *Dec. 10, 2019

(54) COMPOSITIONS AND METHODS FOR INHIBITING EXPRESSION OF FACTOR V

(71) Applicant: Alnylam Pharmaceuticals, Inc., Cambridge, MA (US)

(72) Inventors: Hans-Peter Vornlocher, Bayreuth (DE); John M. Maraganore, Charlestown, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/676,874

(22) Filed: Aug. 14, 2017

(65) Prior Publication Data
US 2018/0127749 A1   May 10, 2018

Related U.S. Application Data

(63) Continuation of application No. 15/241,025, filed on Aug. 18, 2016, now abandoned, which is a continuation of application No. 14/155,239, filed on Jan. 14, 2014, now Pat. No. 9,441,225, which is a continuation of application No. 13/010,300, filed on Jan. 20, 2011, now Pat. No. 8,658,782, which is a continuation of application No. 12/093,235, filed as application No. PCT/US2006/043271 on Nov. 7, 2006, now abandoned.

(60) Provisional application No. 60/735,759, filed on Nov. 9, 2005.

(51) Int. Cl.
| | |
|---|---|
| *C12N 15/11* | (2006.01) |
| *C12N 15/113* | (2010.01) |
| *A61K 48/00* | (2006.01) |
| *A61K 47/54* | (2017.01) |

(52) U.S. Cl.
CPC .......... *C12N 15/113* (2013.01); *A61K 47/554* (2017.08); *A61K 48/00* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 6,083,905 A | 7/2000 | Voorberg et al. | |
| 6,830,884 B1 | 12/2004 | Hafner et al. | |
| 7,427,605 B2 | 9/2008 | Davis et al. | |
| 7,718,629 B2 | 5/2010 | Bumcrot et al. | |
| 2003/0143732 A1 | 7/2003 | Fosnaugh et al. | |
| 2003/0170891 A1 | 9/2003 | McSwiggen | |
| 2004/0192626 A1 | 9/2004 | McSwiggen et al. | |
| 2004/0259247 A1 | 12/2004 | Tuschl et al. | |
| 2005/0107325 A1 | 5/2005 | Manoharan et al. | |
| 2005/0176667 A1 | 8/2005 | Vornlocher | |
| 2006/0068405 A1 | 3/2006 | Diber et al. | |
| 2006/0263435 A1 | 11/2006 | Davis et al. | |
| 2007/0004664 A1 | 1/2007 | McSwiggen et al. | |
| 2007/0031844 A1 | 2/2007 | Khvorova et al. | |
| 2007/0054275 A1 | 3/2007 | Dogulu et al. | |
| 2007/0065844 A1 | 3/2007 | Golub et al. | |
| 2007/0281899 A1 | 12/2007 | Bumcrot et al. | |
| 2009/0149403 A1 | 6/2009 | MacLachlan et al. | |
| 2011/0015250 A1 | 1/2011 | Bumcrot et al. | |
| 2012/0244207 A1 | 9/2012 | Fitzgerald et al. | |

FOREIGN PATENT DOCUMENTS

| | | |
|---|---|---|
| WO | WO 0123612 A2 | 4/2001 |
| WO | WO 2004/080406 A2 | 9/2004 |
| WO | WO 2004/090108 A2 | 10/2004 |
| WO | WO 2005/007843 A2 | 1/2005 |
| WO | WO 2010/147992 A1 | 12/2010 |

OTHER PUBLICATIONS

Agrawal, S., et al., "Antisense oligonucleotides: towards clinical trials." Trends in Biotechnology. Oct. 1996, vol. 14, pp. 376-387.
Amarzguioui, M., et al., "Tolerance for mutations and chemical modifications in a siRNA," Nucleic Acids Research, 2003, pp. 589-595, vol. 31, No. 2.
Bass, B., "The short answer," Nature, May 24, 2001, pp. 428-429, vol. 411.
Braun, et al., "Population study of the G1691 a mutation (R506Q, FV Leiden) in the human factor V gene that is associated with resistance to activated protein C," 1996, Human Genetics, vol. 97, pp. 263-264.
Canadian Intellectual Property Office, Requisition by the Examiner, Canadian Patent Application No. 2,626,690, Nov. 9, 2012, 3 Pages.
Communication Pursuant to Article 94(3) EPC for European Patent Application No. EP 11002061.7, dated Feb. 21, 2013, 4 Pages.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in Drosophila Melanogaster Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.

(Continued)

*Primary Examiner* — Dana H Shin
(74) *Attorney, Agent, or Firm* — Goodwin Procter LLP

(57) ABSTRACT

The invention relates to a double-stranded ribonucleic acid (dsRNA) for inhibiting the expression of Factor V, comprising an antisense strand having a nucleotide sequence which is less that 25 nucleotides in length and which is substantially complementary to at least a part of Factor V. The invention also relates to a pharmaceutical composition comprising the dsRNA together with a pharmaceutically acceptable carrier; methods for treating diseases caused by the expression of Factor V using the pharmaceutical composition; and methods for inhibiting the expression of Factor V in a cell.

14 Claims, No Drawings
Specification includes a Sequence Listing.

(56) References Cited

OTHER PUBLICATIONS

European Search Report dated Aug. 10, 2011, for European Patent Application No. EP 11002061.7, 6 pages.

European Search Report, European Patent Application No. EP 06837014.7, dated Sep. 21, 2009 6 pages.

Examiner's First Report dated Sep. 15, 2010, for Australian Patent Application No. AU 2006311730, 2 pages.

Fire, A., "RNA-triggered Gene Silencing," Trends in Genetics, Sep. 1999, pp. 358-363, vol. 15, No. 9.

Fire, A., et al., "Potent and Specific Genetic Interference by Double Stranded RNA in Caenorhabditis elegans," Nature, Feb. 19, 1998, pp. 806-811, vol. 391.

Hornung, V., et al., "Sequence-specific potent induction of IFN-α by short interfering RNA in plasmacytoid dendritic cells throughTLR7," Nature Medicine, Mar. 2005, pp. 263-270, vol. 11, No. 3.

Naito, et al., "siDirect: highly effective, target-specific siRNA design software for mammalian RNA interference," 2004, Nucleic Acids Research, vol. 32, pp. W124-W129.

Office Action for U.S. Appl. No. 12/093,235, dated May 19, 2010, 11 Pages.

Office Action for U.S. Appl. No. 12/093,235, dated Oct. 20, 2010, 12 Pages.

Office Action for U.S. Appl. No. 13/010,300, dated Jan. 25, 2012, 19 Pages.

Office Action for U.S. Appl. No. 13/010,300, dated Jun. 14, 2012, 16 Pages.

Office Action for U.S. Appl. No. 13/010,300, dated May 3, 2013, 13 Pages.

Office Action dated Jul. 4, 2011, for Canadian Patent Application No. CA 2,626,690, 3 pages.

PCT International Search Report and Written Opinion, PCT/US2006/043271, dated Mar. 5, 2008, 8 Pages.

Price, et al., "Factor V Leiden mutation and the risks for thromboembolic disease: A clinical perspective," 1997, Annals of Internal Medicine, vol. 127, pp. 895-903.

Reynolds, et al. (2004) "Rational siRNA design for RNA interference," Nature Biotechnology, vol. 22, No. 3, pp. 326-330.

Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.

Rose, S., et al., "Functional polarity is introduced by Dicer processing of short substrate RNAs," Nucleic Acids Research, 2005, pp. 4140-4156, vol. 33, No. 13.

Tuschl T., "RNA Interference and Small Interfering RNAs" Chembiochem, 2001, pp. 239-245, vol. 2.

Tuschl, T., "Expanding small RNA interference," Nature Biotechnology, May 2002, pp. 446-448, vol. 20.

Tuschl, T., "Functional genomics: RNA sets the standard," Nature, Jan. 16, 2003, vol. 421, No. 6920, pp. 220-221.

Tuschl, T., "Mammalian RNA Interference," RNAi, A Guide to Gene Silencing, Chapter 13, G.J. Hannon (ed,), 2003, pp. 265-295.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., et al., "Targeted mRNA Degradation by Double-Stranded RNA In Vitro," Genes & Development, 1999, pp. 3191-3197, vol. 13.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

Weil, et al (2002) "Targeting the Kinesin Eg5 to Monitor siRNA Transfection in Mammalian Cells," *Biotechniques* 33(6):1244-1248.

Zimmerman, et al. (2006) "RNAi-mediated gene silencing in non-human primates," *Nature*, vol. 441, May 4:111-114.

COMPOSITIONS AND METHODS FOR INHIBITING EXPRESSION OF FACTOR V

CROSS-REFERENCE TO RELATED APPLICATIONS

This application is a continuation of U.S. application Ser. No. 15/241,025, filed on Aug. 18, 2016, which is a continuation of U.S. application Ser. No. 14/155,239, filed Jan. 14, 2014 now U.S. Pat. No. 9,441,225, issued Sep. 13, 2016, which is a continuation of U.S. application Ser. No. 13/010,300, filed Jan. 20, 2011, now U.S. Pat. No. 8,658,782, issued Feb. 25, 2014, which is a continuation of U.S. application Ser. No. 12/093,235, with a 371c filing date of Nov. 5, 2008 (abandoned), which is a National Stage under 35 U.S.C. § 371 of International Application No. PCT/US2006/043271, filed Nov. 7, 2006, which claims the benefit of U.S. Provisional Application No. 60/735,759, filed Nov. 9, 2005, each of which is incorporated herein by reference, in its entirety.

SEQUENCE LISTING

The instant application contains a Sequence Listing with 76 sequences which has been submitted via EFS-Web and is hereby incorporated by reference in its entirety. Said ASCII copy, created on Aug. 14, 2017, is named 38224_US_CRF_sequencelisting.txt, and is 45,056 bytes in size.

FIELD OF THE INVENTION

This invention relates to double-stranded ribonucleic acid (dsRNA), and its use in mediating RNA interference to inhibit the expression of the Factor V Leiden mutant gene and the use of the dsRNA to treat thrombophilia.

BACKGROUND OF THE INVENTION

Factor V Leiden thrombophilia is characterized by a poor anticoagulant response to activated protein C (APC) and an increased risk of venous thromboembolism. The term "factor V Leiden" refers to the specific G-to-A substitution at nucleotide 1691 in the gene for factor V that predicts a single amino acid replacement (Arg506Gln) at one of three APC cleavage sites in the factor Va molecule. Factor V Leiden is inactivated at a rate approximately ten times slower than normal factor V and persists longer in the circulation, resulting in increased thrombin generation and a mild hypercoagulable state reflected by elevated levels of prothrombin fragment F1+2 and other activated coagulation markers. Individuals heterozygous for the factor V Leiden mutation have a slightly increased risk for venous thrombosis; homozygous individuals have a much greater thrombotic risk.

Factor V Leiden is the most common hereditary blood coagualtion disorder in the United States. It is present 5% of the in the Caucasian population and 1.2% of the African American population.

Factor V Leiden increases the risk of venous thrombosis 3-8 fold for heterozygous (one damaged gene inherited) and substantially more, 30-140 fold, for homozygous (two damaged genes inherited) individuals.

Deep venous thrombosis with the attendant risk of pulmonary embolism and post phlebitic syndrome is a frequent complication in older patients who have undergone surgery, suffered trauma or who have serious illness such as malignancy or sepsis. In any category patients who are 40 years of age or older are considered to be at greatest risk. Also the longer the period of immobilization the greater the risk of DVT. Other factors that have been reported to contribute to development of DVT are obesity, prior history of DVT and smoking. While none of these factors alone or in combination will identify individual patients who will develop DVT, the incidence of DVT during the postoperative or posttraumatic period does correlate with the condition.

DVT has three major risks for the patient, two acute and one delayed. The acute problems are leg swelling, pain and tenderness and the risk of pulmonary embolism. In pulmonary embolism part of the thrombus breaks away and is carried to the lung where it can block a pulmonary artery causing respiratory distress in proportion to the amount of blockage, i.e., to the size of the embolus. Large emboli that block both pulmonary arteries cause immediate death. The delayed problem is the post phlebitic syndrome in which there is lower extremity pain or cramps at rest, leg edema, skin changes and skin breakdown causing chronic ulcers of the lower extremity. Clinicians have long known that the post phlebitic syndrome develops in a large percentage of patients who have DVT, especially those having extensive thrombus formation. Objective studies have shown that 1-10 years following the occurrence of DVT as much as 80% of patients will have both symptoms and abnormal venous hemodynamics (Lindner et al, 1986; Markel et at, 1992). While the post phlebitic syndrome is less dramatic than a major pulmonary embolus, it is a serious condition for the patients, resulting in much discomfort and expense.

In some patients groups DVT and pulmonary embolism are major causes of morbidity and mortality. Thromboembolism is a major cause of morbidity and mortality in patients with spinal cord injury. The prevalence of DVT has been reported to range from 47% (Merli et al, 1988) to 78% (Green et al, 1982). Of these 1 to 2% will die of pulmonary embolism (Green, 1991). Thrombosis usually occurs 1 to 3 weeks after injury, with a peak between days 7 and 9. The incidence of thromboembolic complications in patients undergoing surgery for fractured hip is high, ranging from about 40-60% (Powers et al, 1989; Fordyce and Ling, 1992; Turpie, 1991; Levine et al, 1991; Hull et al, 1990). In patients undergoing knee arthroplasty the incidence of DVT ranges from about 50% to 85% (Stulberg et al, 1984; Leclerc et al, 1992; Wilson et al, 1992). In gynecologic malignancy the incidence of DVT was 35% (Clarke-Person et al, 1984). The incidence of DVT in patients undergoing elective general abdominal surgery was about 9% in those without malignancy and about 11% in those with malignancies (Bergqvist et al, Seminars in Thromb & Hemost 16 Suppl 19-24, 1990).

For about 50 years efforts to prevent development of DVT and to treat those that do develop have focused on the judicious use of anticoagulants, first through full doses of oral anticoagulants and more recently through low dose heparin prophylaxis (Gallus, 1990). The aim has been to achieve a helpful degree of anticoagulation (prolongation of the clotting process) without causing hemorrhage. Low dose heparin has become the standard of comparison for other preventive methods since it is relatively safe and simple and prevents approximately 65% of subclinical thrombi found by leg scanning after elective general surgery. Postoperative death from pulmonary emboli may be reduced by 65% also.

However, there are clinical situations in which low dose heparin is less effective, most notable after orthopedic surgery where the use of more complex regimens, including adjusted dose heparin and various schedules of warfarin prophylaxis are appropriate. Several studies have shown that higher levels of anticoagulation are more effective than lower ones. However, if anticoagulation is too high, bleeding complications result.

Recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of the Factor V Leiden mutant gene in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Despite significant advances in the field of RNAi and advances in the treatment of thrombophilia, there remains a need for an agent that can selectively and efficiently silence the Factor V Leiden mutant gene using the cell's own RNAi machinery that has both high biological activity and in vivo stability, and that can effectively inhibit expression of a target Factor V Leiden mutant gene for use in treating thrombophilia.

SUMMARY OF THE INVENTION

The invention provides double-stranded ribonucleic acid (dsRNA), as well as compositions and methods for inhibiting the expression of the Factor V Leiden mutant gene in a cell or mammal using such dsRNA. The invention also provides compositions and methods for treating pathological conditions and diseases caused by the expression of the Factor V Leiden mutant gene, such as in thrombophilia. The dsRNA of the invention comprises an RNA strand (the antisense strand) having a region which is less than 30 nucleotides in length and is substantially complementary to at least part of an mRNA transcript of the Factor V Leiden mutant gene.

In embodiment, the invention provides double-stranded ribonucleic acid (dsRNA) molecules for inhibiting the expression of the Factor V Leiden mutant gene. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoding Factor V Leiden mutant, and the region of complementarity is less than 30 nucleotides in length. The dsRNA, upon contacting with a cell expressing the Factor V Leiden mutant, inhibits the expression of the Factor V Leiden mutant gene by at least 40%.

For example, the dsRNA molecules of the invention can be comprised of a first sequence of the dsRNA that is selected from the group consisting of the sense sequences of Table 1 and the second sequence is selected from the group consisting of the antisense sequences of Table 1. The dsRNA molecules of the invention can be comprised of naturally occurring nucleotides or can be comprised of at least one modified nucleotide, such as a 2'-O-methyl modified nucleotide, a nucleotide comprising a 5'-phosphorothioate group, and a terminal nucleotide linked to a cholesteryl derivative or dodecanoic acid bisdecylamide group. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of the sense sequences of Table 1 and the second sequence is selected from the group consisting of the antisense sequences of Table 1.

In another embodiment, the invention provides a cell comprising one of the dsRNAs of the invention. The cell is preferably a mammalian cell, such as a human cell.

In another embodiment, the invention provides a pharmaceutical composition for inhibiting the expression of the Factor V Leiden mutant gene in an organism, comprising one or more of the dsRNA of the invention and a pharmaceutically acceptable carrier.

In another embodiment, the invention provides a method for inhibiting the expression of the Factor V Leiden mutant gene in a cell, comprising the following steps:

(a) introducing into the cell a double-stranded ribonucleic acid (dsRNA), wherein the dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of a mRNA encoding Factor V Leiden mutant, and wherein the region of complementarity is less than 30 nucleotides in length and wherein the dsRNA, upon contact with a cell expressing the Factor V Leiden mutant, inhibits expression of the Factor V Leiden mutant gene by at least 20%; and (b) maintaining the cell produced in step (a) for a time sufficient to obtain degradation of the mRNA transcript of the Factor V Leiden mutant gene, thereby inhibiting expression of the Factor V Leiden mutant gene in the cell.

In another embodiment, the invention provides methods for treating, preventing or managing thrombophilia comprising administering to a patient in need of such treatment, prevention or management a therapeutically or prophylactically effective amount of one or more of the dsRNAs of the invention.

TABLE 1

| Duplex identifier | Sense strand sequence (5'-3') | SEQ ID NO: | Antisense strand sequence (5'-3') | SEQ ID NO: |
|---|---|---|---|---|
| wt1 | cccuggacaggcgaggaauTT | 1 | auuccucgccuguccagggTT | 2 |
| wt2 | ccuggacaggcgaggaauaTT | 3 | uauuccucgccuguccaggTT | 4 |
| wt3 | cuggacaggcgaggaauacTT | 5 | guauuccucgccuguccagTT | 6 |

TABLE 1-continued

| Duplex identifier | Sense strand sequence (5'-3') | SEQ ID NO: | Antisense strand sequence (5'-3') | SEQ ID NO: |
|---|---|---|---|---|
| wt4 | uggacaggcgaggaauacaTT | 7 | uguauuccucgccuguccaTT | 8 |
| wt5 | ggacaggcgaggaauacagTT | 9 | cuguauuccucgccuguccTT | 10 |
| wt6 | gacaggcgaggaauacagaTT | 11 | ucuguauuccucgccugucTT | 12 |
| wt7 | acaggcgaggaauacagagTT | 13 | cucuguauuccucgccuguTT | 14 |
| wt8 | caggcgaggaauacagaggTT | 15 | ccucuguauuccucgccugTT | 16 |
| wt9 | aggcgaggaauacagagggTT | 17 | cccucuguauuccucgccuTT | 18 |
| wt10 | ggcgaggaauacagagggcTT | 19 | gcccucuguauuccucgccTT | 20 |
| wt11 | gcgaggaauacagagggcaTT | 21 | ugcccucuguauuccucgcTT | 22 |
| wt12 | cgaggaauacagagggcagTT | 23 | cugcccucuguauuccucgTT | 24 |
| wt13 | gaggaauacagagggcagcTT | 25 | gcugcccucuguauuccucTT | 26 |
| wt14 | gcagaucccuggacaggcaTT | 27 | ugccuguccagggaucugcTT | 28 |
| wt15 | cagaucccuggacaggcaaTT | 29 | uugccuguccagggaucugTT | 30 |
| wt16 | agaucccuggacaggcaagTT | 31 | cuugccuguccagggaucuTT | 32 |
| wt17 | gaucccuggacaggcaaggTT | 33 | ccuugccuguccagggaucTT | 34 |
| wt18 | aucccuggacaggcaaggaTT | 35 | uccuugccuguccagggauTT | 36 |
| wt19 | ucccuggacaggcaaggaaTT | 37 | uuccuugccuguccagggaTT | 38 |
| mut1 | ccccuggacaggcaaggaauTT | 39 | auuccuugccuguccagggTT | 40 |
| mut2 | ccuggacaggcaaggaauaTT | 41 | uauuccuugccuguccaggTT | 42 |
| mut3 | cuggacaggcaaggaauacTT | 43 | guauuccuugccuguccagTT | 44 |
| mut4 | uggacaggcaaggaauacaTT | 45 | uguauuccuugccuguccaTT | 46 |
| mut5 | ggacaggcaaggaauacagTT | 47 | cuguauuccuugccuguccTT | 48 |
| mut6 | gacaggcaaggaauacagaTT | 49 | ucuguauuccuugccugucTT | 50 |
| mut7 | acaggcaaggaauacagagTT | 51 | cucuguauuccuugccuguTT | 52 |
| mut8 | caggcaaggaauacagaggTT | 53 | ccucuguauuccuugccugTT | 54 |
| mut9 | aggcaaggaauacagagggTT | 55 | cccucuguauuccuugccuTT | 56 |
| mut10 | ggcaaggaauacagagggcTT | 57 | gcccucuguauuccuugccTT | 58 |
| mut11 | gcaaggaauacagagggcaTT | 59 | ugcccucuguauuccuugcTT | 60 |
| mut12 | caaggaauacagagggcagTT | 61 | cugcccucuguauuccuugTT | 62 |
| mut13 | aaggaauacagagggcagcTT | 63 | gcugcccucuguauuccuuTT | 64 |
| mut14 | acaggcaaggaauacagagtt | 65 | cucuguauuccuugccugutt | 66 |
| mut15 | caggcaaggaauacagaggtt | 67 | ccucuguauuccuugccugtt | 68 |
| mut16 | aggcaaggaauacagagggtt | 69 | cccucuguauuccuugccutt | 70 |
| mut17 | ggcaaggaauacagagggctt | 71 | gcccucuguauuccuugcctt | 72 |
| mut18 | gcaaggaauacagagggcatt | 73 | ugcccucuguauuccuugctt | 74 |
| mut19 | caaggaauacagagggcagtt | 75 | cugcccucuguauuccuugtt | 76 |

In another embodiment, the invention provides vectors for inhibiting the expression of the Factor V Leiden mutant gene in a cell, comprising a regulatory sequence operably linked to a nucleotide sequence that encodes at least one strand of one of the dsRNA of the invention.

In another embodiment, the invention provides a cell comprising a vector for inhibiting the expression of the Factor V Leiden mutant gene in a cell. The vector comprises a regulatory sequence operably linked to a nucleotide sequence that encodes at least one strand of one of the dsRNA of the invention.

BRIEF DESCRIPTION OF THE FIGURES

No Figures are presented

DETAILED DESCRIPTION OF THE INVENTION

The invention provides double-stranded ribonucleic acid (dsRNA), as well as compositions and methods for inhibiting the expression of the Factor V Leiden mutant gene in a cell or mammal using the dsRNA. The invention also provides compositions and methods for treating pathological conditions and diseases in a mammal caused by the expression of the Factor V Leiden mutant gene using dsRNA. dsRNA directs the sequence-specific degradation of mRNA through a process known as RNA interference (RNAi). The process occurs in a wide variety of organisms, including mammals and other vertebrates.

The dsRNA of the invention comprises an RNA strand (the antisense strand) having a region which is less than 30 nucleotides in length and is substantially complementary to at least part of an mRNA transcript of the Factor V Leiden mutant gene. The use of these dsRNAs enables the targeted degradation of mRNAs of genes that are implicated in thrombophilia response in mammals. Using cell-based and animal assays, the present inventors have demonstrated that very low dosages of these dsRNA can specifically and efficiently mediate RNAi, resulting in significant inhibition of expression of the Factor V Leiden mutant gene. Thus, the methods and compositions of the invention comprising these dsRNAs are useful for treating thrombophilia.

The following detailed description discloses how to make and use the dsRNA and compositions containing dsRNA to inhibit the expression of a target Factor V Leiden mutant gene, as well as compositions and methods for treating diseases and disorders caused by the expression of Factor V Leiden mutant, such as thrombophilia. The pharmaceutical compositions of the invention comprise a dsRNA having an antisense strand comprising a region of complementarity which is less than 30 nucleotides in length and is substantially complementary to at least part of an RNA transcript of the Factor V Leiden mutant gene, together with a pharmaceutically acceptable carrier.

Accordingly, certain aspects of the invention provide pharmaceutical compositions comprising the dsRNA of the invention together with a pharmaceutically acceptable carrier, methods of using the compositions to inhibit expression of the Factor V Leiden mutant gene, and methods of using the pharmaceutical compositions to treat diseases caused by expression of the Factor V Leiden mutant gene.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

By "Factor V Leiden mutant" as used herein is meant, any mutation in the Factor V gene, protein, peptide, or polypeptide. The term "factor V Leiden" generally refers to the specific G-to-A substitution at nucleotide 1691 in the gene for factor V that predicts a single amino acid replacement (Arg506Gln) at one of three APC cleavage sites in the factor Va molecule.

As used herein, "target sequence" refers to a contiguous portion of the nucleotide sequence of an mRNA molecule formed during the transcription of the Factor V Leiden mutant gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but preferably not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding Factor V Leiden mutant). For example, a polynucleotide is complementary to at least a part of a Factor V Leiden mutant mRNA if the sequence is substantially complementary to a non-interrupted portion of a mRNA encoding Factor V Leiden mutant.

The term "double-stranded RNA" or "dsRNA", as used herein, refers to a ribonucleic acid molecule, or complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein.

Where the region of complementarity is not fully complementary to the target sequence, the mismatches are most tolerated in the terminal regions and, if present, are preferably in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to the Factor V Leiden mutant gene, herein refer to the at least partial suppression of the expression of the Factor V Leiden mutant gene, as manifested by a reduction of the amount of mRNA transcribed from the Factor V Leiden mutant gene which may be isolated from a first cell or group of cells in which the Factor V Leiden mutant gene is transcribed and which has or have been treated such that the expression of the Factor V Leiden mutant gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to Factor V Leiden mutant gene transcription, e.g. the amount of protein encoded by the Factor V Leiden mutant gene which is secreted by a cell, or the number of cells displaying a certain phenotype, e.g apoptosis. In principle, Factor V Leiden mutant gene silencing may be determined in any cell expressing the target, either constitutively or by genomic engineering, and by any appropriate assay. However, when a reference is needed in order to determine whether a given siRNA inhibits the expression of the Factor V Leiden mutant gene by a certain degree and therefore is encompassed by the instant invention, the assay provided in the Examples below shall serve as such reference.

For example, in certain instances, expression of the Factor V Leiden mutant gene is suppressed by at least about 20%, 25%, 35%, or 50% by administration of the double-stranded oligonucleotide of the invention. In a preferred embodiment, the Factor V Leiden mutant gene is suppressed by at least about 60%, 70%, or 80% by administration of the double-stranded oligonucleotide of the invention. In a more preferred embodiment, the Factor V Leiden mutant gene is suppressed by at least about 85%, 90%, or 95% by administration of the double-stranded oligonucleotide of the invention. In a most preferred embodiment, the Factor V Leiden mutant gene is suppressed by at least about 98%, 99% or more by administration of the double-stranded oligonucleotide of the invention.

The terms "treat", "treatment", and the like, refer to relief from or alleviation of thrombophilia. In the context of the present invention insofar as it relates to any of the other conditions recited herein below (other than thrombophilia), the terms "treat", "treatment", and the like mean to relieve or alleviate at least one symptom associated with such condition, or to slow or reverse the progression of such condition.

As used herein, the phrases "therapeutically effective amount" and "prophylactically effective amount" refer to an amount that provides a therapeutic benefit in the treatment, prevention, or management of thrombophilia or an overt symptom of thrombophilia. The specific amount that is therapeutically effective can be readily determined by ordinary medical practitioner, and may vary depending on factors known in the art, such as, e.g. the type of thrombophilia, the patient's history and age, the stage of thrombophilia, and the administration of other anti-thrombophilia agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-Stranded Ribonucleic Acid (dsRNA)

In one embodiment, the invention provides double-stranded ribonucleic acid (dsRNA) molecules for inhibiting the expression of the Factor V Leiden mutant gene in a cell or mammal, wherein the dsRNA comprises an antisense strand comprising a region of complementarity which is complementary to at least a part of an mRNA formed in the expression of the Factor V Leiden mutant gene, and wherein the region of complementarity is less than 30 nucleotides in length and wherein said dsRNA, upon contact with a cell expressing said Factor V Leiden mutant gene, inhibits the expression of said Factor V Leiden mutant gene by at least 20%. The dsRNA comprises two RNA strands that are sufficiently complementary to hybridize to form a duplex structure. One strand of the dsRNA (the antisense strand) comprises a region of complementarity that is substantially complementary, and preferably fully complementary, to a target sequence, derived from the sequence of an mRNA formed during the expression of the Factor V Leiden mutant gene, the other strand (the sense strand) comprises a region which is complementary to the antisense strand, such that the two strands hybridize and form a duplex structure when combined under suitable conditions. Preferably, the duplex structure is between 15 and 30, more preferably between 18 and 25, yet more preferably between 19 and 24, and most preferably between 21 and 23 base pairs in length. Similarly, the region of complementarity to the target sequence is between 15 and 30, more preferably between 18 and 25, yet more preferably between 19 and 24, and most preferably between 21 and 23 nucleotides in length. The dsRNA of the invention may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In a preferred embodiment, the Factor V Leiden mutant gene is the human Factor V Leiden mutant gene. In specific embodiments, the antisense strand of the dsRNA comprises the sense sequences of Table 1 and the second sequence is selected from the group consisting of the antisense sequences of Table 1.

In further embodiments, the dsRNA comprises at least one nucleotide sequence selected from the groups of sequences provided in Table 1. In other embodiments, the dsRNA comprises at least two sequences selected from this group, wherein one of the at least two sequences is complementary to another of the at least two sequences, and one of the at least two sequences is substantially complementary to a sequence of an mRNA generated in the expression of the Factor V Leiden mutant gene. Preferably, the dsRNA comprises two oligonucleotides, wherein one oligonucleotide is described by Table 1 and the second oligonucleotide is described Table 1

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Table 1, the dsRNAs of the invention can comprise at least one strand of a length of minimally 21 nt. It can be reasonably expected that shorter dsRNAs comprising one of the sequences of Table 1 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of Table 1, and differing in their ability to inhibit the expression of the Factor V Leiden mutant gene in a FACS assay as described herein below by not more than 5, 10, 15, 20, 25, or 30% inhibition from a dsRNA comprising the full sequence, are contemplated by the invention.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the Factor V Leiden mutant gene, the dsRNA preferably does not contain any mismatch within the central 13 nucleotides. The methods described within the invention can be used to determine whether a dsRNA containing a mismatch to a target sequence is effective in inhibiting the expression of the Factor V Leiden mutant gene. Consideration of the efficacy of dsRNAs with mismatches in inhibiting expression of the Factor V Leiden mutant gene is important, especially if the particular region of complementarity in the Factor V Leiden mutant gene is known to have polymorphic sequence variation within the population.

In one embodiment, at least one end of the dsRNA has a single-stranded nucleotide overhang of 1 to 4, preferably 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Preferably, the single-stranded overhang is located at the 3'-terminal end of the antisense strand or, alternatively, at the 3'-terminal end of the sense strand. The dsRNA may also have a blunt end, preferably located at the 5'-end of the antisense strand. Such dsRNAs have improved stability and inhibitory activity, thus allowing administration at low dosages, i.e., less than 5 mg/kg body weight of the recipient per day. Preferably, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, *Biochem.* (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds. Table 1 provides examples of modified RNAi agents of the invention.

In certain embodiments, a chemical bond may be formed by means of one or several bonding groups, wherein such bonding groups are preferably poly-(oxyphosphinicooxy-1,3-propandiol)- and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

In yet another embodiment, the nucleotides at one or both of the two single strands may be modified to prevent or inhibit the activation of cellular enzymes, such as, for example, without limitation, certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, preferably by a 2'-amino or a 2'-methyl group. Also, at least one nucleotide may be modified to form a locked nucleotide. Such locked nucleotide contains a methylene bridge that connects the 2'-oxygen of ribose with the 4'-carbon of ribose. Oligonucleotides containing the locked nucleotide are described in Koshkin, A. A., et al., *Tetrahedron* (1998), 54: 3607-3630) and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, *Chem. Biol.* (2001), 8:1-7).

Conjugating a ligand to a dsRNA can enhance its cellular absorption as well as targeting to a particular tissue. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptormediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540. Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, an dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In the ligand-conjugated dsRNA and ligand-molecule bearing sequence-specific linked nucleosides of the invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the invention include, but are not limited to, 2'-aminoalkoxy-5'-ODMT-nucleosides, 2'-6-aminoalkylamino-5'-ODMT-nucleosides, 5'-6-aminoalkoxy-2'-deoxy-nucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron*, 1992, 48:2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.*, 1994, 35:7821; Verhart and Tesser, *Rec. Trav. Chim. Pays-Bas*, 1987, 107:621).

Additional amino-protecting groups include, but are not limited to, carbamate protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the invention.

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., *Innovations and Perspectives in solid-phase Synthesis, 3rd International Symposium,* 1994, Ed. Roger Epton, Mayflower Worldwide, 115-124]; Azhayev, A. V. *Tetrahedron* 1999, 55, 787-800; and Azhayev and Antopolsky *Tetrahedron* 2001, 57, 4977-4986. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. *J. Am. Chem. Soc.* 2003, 125, 2380.

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced dsRNA activity when compared to like dsRNA compounds that are not conjugated.

The aralkyl-ligand-conjugated oligonucleotides of the invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

Specific examples of preferred modified oligonucleotides envisioned for use in the ligand-conjugated oligonucleotides of the invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497.

Some preferred embodiments of the invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand-conjugated oligonucleotides of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering,* pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications,* pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,808,027; all of which are hereby incorporated by reference.

In certain embodiments, the oligonucleotides employed in the ligand-conjugated oligonucleotides of the invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_n$O]$_m CH_3$, O$(CH_2)_n$OCH$_3$, O$(CH_2)_n$NH$_2$, O$(CH_2)_n$CH$_3$, O$(CH_2)_n$ONH$_2$, and O$(CH_2)_n$ON[$(CH_2)_n$CH$_3$]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. a preferred modification includes 2'-methoxyethoxy [2'-O—$CH_2CH_2OCH_3$, also known as 2'-O-(2-methoxyethyl) or 2'-MOE] (Martin et al., *Helv. Chim. Acta*, 1995, 78, 486), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. Pat. No. 6,127,533, filed on Jan. 30, 1998, the contents of which are incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula (O-alkyl)$_m$, wherein m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9:93); Ravasio et al. (*J. Org. Chem.* 1991, 56:4329); and Delgardo et. al. (*Critical Reviews in Therapeutic Drug Carrier Systems* 1992, 9:249), each of which is hereby incorporated by reference in its entirety. Further sugar modifications are disclosed by Cook (*Anti-thrombophilia Drug Design*, 1991, 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the invention include 2'-SR and 2'-NR2 groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (*J. Org. Chem.*, 1997, 62:3415-3420). 2'-NR nucleosides are disclosed by Goettingen, M., *J. Org. Chem.*, 1996, 61, 6273-6281; and Polushin et al., *Tetrahedron Lett.*, 1996, 37, 3227-3230. Further representative 2'-substituent groups amenable to the invention include those having one of formula I or II:

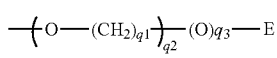

I

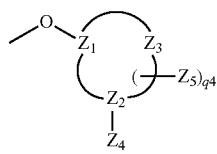

II wherein,

E is $C_1$-$C_{10}$ alkyl, $N(Q_3)(Q_4)$ or $N=C(Q_3)(Q_4)$; each $Q_3$ and $Q_4$ is, independently, H, $C_1$-$C_{10}$ alkyl, dialkylaminoalkyl, a nitrogen protecting group, a tethered or untethered conjugate group, a linker to a solid support; or $Q_3$ and $Q_4$, together, form a nitrogen protecting group or a ring structure optionally including at least one additional heteroatom selected from N and O;

$q_1$ is an integer from 1 to 10;
$q_2$ is an integer from 1 to 10;
$q_3$ is 0 or 1;
$q_4$ is 0, 1 or 2;

each $Z_1$, $Z_2$ and $Z_3$ is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;

$Z_4$ is $OM_1$, $SM_1$, or $N(M_1)_2$; each $M_1$ is, independently, H, $C_1$-$C_8$ alkyl, $C_1$-$C_8$ haloalkyl, C(=NH)N(H)$M_2$, C(=O)N(H)$M_2$ or OC(=O)N(H)$M_2$; $M_2$ is H or $C_1$-$C_8$ alkyl; and $Z_5$ is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, $N(Q_3)(Q_4)$, $OQ_3$, halo, $SQ_3$ or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the invention. Representative substitutions for ring O include, but are not limited to, S, $CH_2$, CHF, and $CF_2$. See, e.g., Secrist et al., Abstract 21, *Program & Abstracts, Tenth International Roundtable, Nucleosides, Nucleotides and their Biological Applications*, Park City, Utah, Sep. 16-20, 1992.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,700,920; and 5,859,221, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci. USA*, 1989, 86, 6553), cholic acid (Manoharan et al., *Bioorg.*

Med. Chem. Lett., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylamino-carbonyl-oxycholesterol moiety (Crooke et al., J. Pharmacol. Exp. Ther., 1996, 277, 923).

Representative United States patents relating to the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

The invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-trityl-thiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate. The use of a cholesterol conjugate is particularly preferred since sucha moiety can increase targeting to tissues in the liver, a site of Factor V protein production.

Alternatively, the molecule being conjugated may be converted into a building block, such as a phosphoramidite, via an alcohol group present in the molecule or by attachment of a linker bearing an alcohol group that may be phosphitylated.

Importantly, each of these approaches may be used for the synthesis of ligand conjugated oligonucleotides. Amino-linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

III. Pharmaceutical Compositions Comprising dsRNA

In one embodiment, the invention provides pharmaceutical compositions comprising a dsRNA, as described herein, and a pharmaceutically acceptable carrier. The pharmaceutical composition comprising the dsRNA is useful for treating a disease or disorder associated with the expression or activity of the Factor V Leiden mutant gene, such as thrombophilia.

The pharmaceutical compositions of the invention are administered in dosages sufficient to inhibit expression of the Factor V Leiden mutant gene. The present inventors have found that, because of their improved efficiency, compositions comprising the dsRNA of the invention can be administered at surprisingly low dosages. A maximum dosage of 5 mg dsRNA per kilogram body weight of recipient per day is sufficient to inhibit or completely suppress expression of the Factor V Leiden mutant gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day or even using continuous infusion. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as thrombophilia. Such models are used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered intraveneously.

For intramuscular, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the Factor V Leiden mutant gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the Factor V Leiden mutant gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

The present invention further provides devices containing the RNAi agents of the present invention, such as devices that come into contact with the blood. Examples of devices that come into contact with blood include vascular grafts, stents, orthopedic prosthesis, cardiac prosthesis, and extracorporeal circulation systems.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs of the invention can be administered in combination with other known agents effective in treatment of thrombophilia. In any event, the administering physician can adjust the amount and timing of dsRNA administration on the basis of results observed using standard measures of efficacy known in the art or described herein.

The RNAi agents of the present invention can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin and simvastatin, HMG CoA synthase inhibitors, etc.) to treat or prevent atherosclerosis. For example, patients suffering from coronary artery disease, and patients subjected to angioplasty procedures, would benefit from coadminstration of fibrinogen receptor antagonists and present RNAi agents.

Methods for Treating Diseases Caused by Expression of the Factor V Leiden Mutant Gene In one embodiment, the invention provides a method for treating a subject having a pathological condition mediated by the expression of the Factor V Leiden mutant gene, such as thrombophilia. In this embodiment, the dsRNA acts as a therapeutic agent for controlling the expression of the Factor V Leiden mutant protein. The method comprises administering a pharmaceutical composition of the invention to the patient (e.g., human), such that expression of the Factor V Leiden mutant gene is silenced. Because of their high specificity, the dsRNAs of the invention specifically target mRNAs of the Factor V Leiden mutant gene.

Thrombophilia

The compounds of the invention are useful in those conditions where anticoagulant therapy or prophylaxis is indicated, including the following.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

The invention thus provides the use of an anti-Factor V Leiden mutant dsRNA administered to a human, particularly by intraveneous administration, for the treatment of thrombophilia The pharmaceutical compositions encompassed by the invention may be administered by any means known in the art including, but not limited to oral or parenteral routes, including intravenous, intramuscular, intraperitoneal, subcutaneous, transdermal, airway (aerosol), nasal, rectal, vaginal and topical (including buccal and sublingual) administration, and epidural administration. In preferred embodiments, the pharmaceutical compositions are administered intraveneously by infusion or injection.

Methods for Inhibiting Expression of the Factor V Leiden Mutant Gene

In yet another aspect, the invention provides a method for inhibiting the expression of the Factor V Leiden mutant gene in a mammal. The method comprises administering a composition of the invention to the mammal such that expression of the target Factor V Leiden mutant gene is silenced. Because of their high specificity, the dsRNAs of the invention specifically target RNAs (primary or processed) of the target Factor V Leiden mutant gene. Compositions and methods for inhibiting the expression of these Factor V Leiden mutant genes using dsRNAs can be performed as described elsewhere herein.

In one embodiment, the method comprises administering a composition comprising a dsRNA, wherein the dsRNA comprises a nucleotide sequence which is complementary to at least a part of an RNA transcript of the Factor V Leiden mutant gene of the mammal to be treated. When the organism to be treated is a mammal such as a human, the composition may be administered by any means known in the art including, but not limited to oral or parenteral routes, including intravenous, intramuscular, intracranial, subcutaneous, transdermal, airway (aerosol), nasal, rectal, vaginal and topical (including buccal and sublingual) administration. In preferred embodiments, the compositions are administered by intraveneous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Gene Walking of the Factor V Leiden Mutant Gene siRNAs were identified in a multi step sequence analysis process in order to design siRNAs targeting the Factor V Leiden mutant gene.

The in silico selected siRNAs are provided in Table 1.

dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3), an appropriately modified solid support was used for RNA synthesis. The modified solid support was prepared as follows:

Diethyl-2-azabutane-1,4-dicarboxylate AA

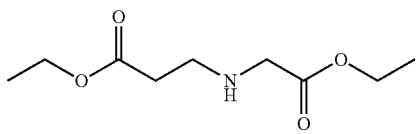

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

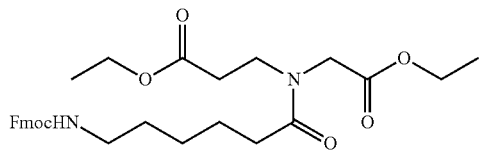

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

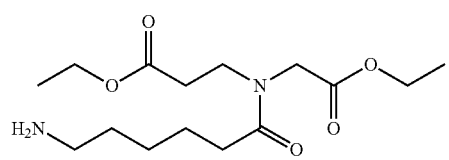

3-{Ethoxycarbonylmethyl-[6-(9H-fluoren-9-ylmethoxycarbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,
4,7,8,9,10,11,12,13,14,15,16,17-tetradecahydro-1H-
cyclopenta[a]phenanthren-3-yloxycarbonylamino]-
hexanoyl}ethoxycarbonylmethyl-amino)-propionic
acid ethyl ester AD

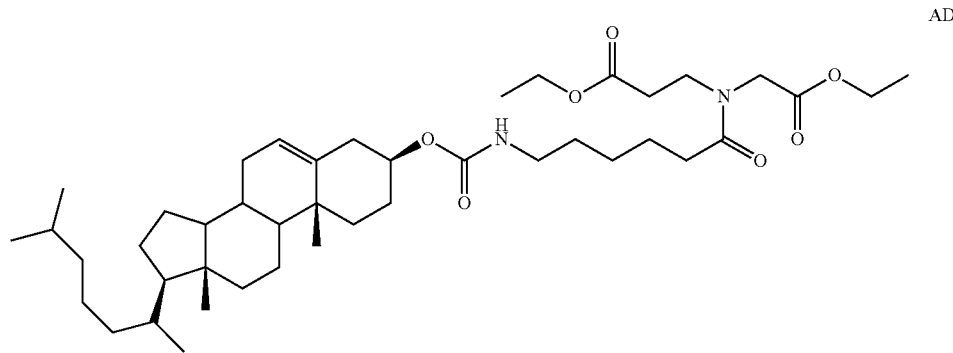 [SMILES: CCOC(=O)CCN(CC(=O)OCC)C(=O)CCCCCNC(=O)O[C@H]1CC[C@@]2(C)C(=CCC3C2CC[C@@]2(C)C3CC[C@@H]2C(C)CCCC(C)C)C1]

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,
4,7,8,9,10,11,12,13,14,15,16,17-tetradecahydro-1H-
cyclopenta[a]phenanthren-3-yloxycarbonylamino]-
hexanoyl}-4-oxo-pyrrolidine-3-carboxylic acid ethyl
ester AE

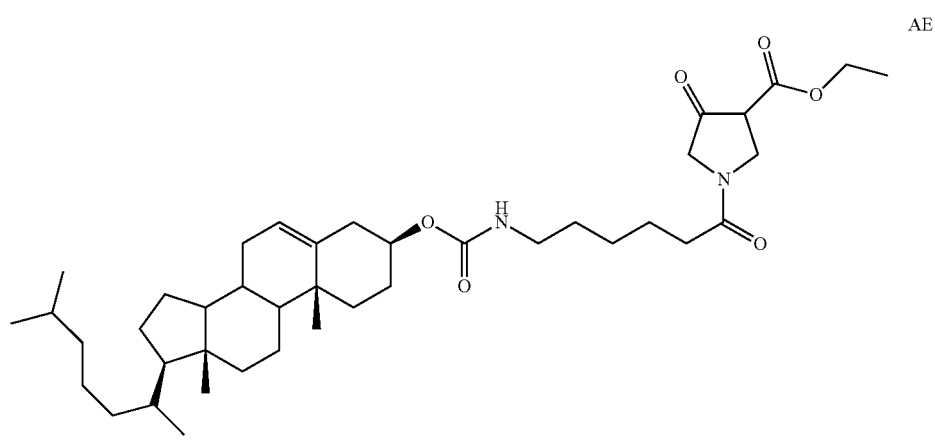 [SMILES: CCOC(=O)C1CN(C(=O)CCCCCNC(=O)O[C@H]2CC[C@@]3(C)C(=CCC4C3CC[C@@]3(C)C4CC[C@@H]3C(C)CCCC(C)C)C2)CC1=O]

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of NaH$_2$PO$_4$.H$_2$O in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

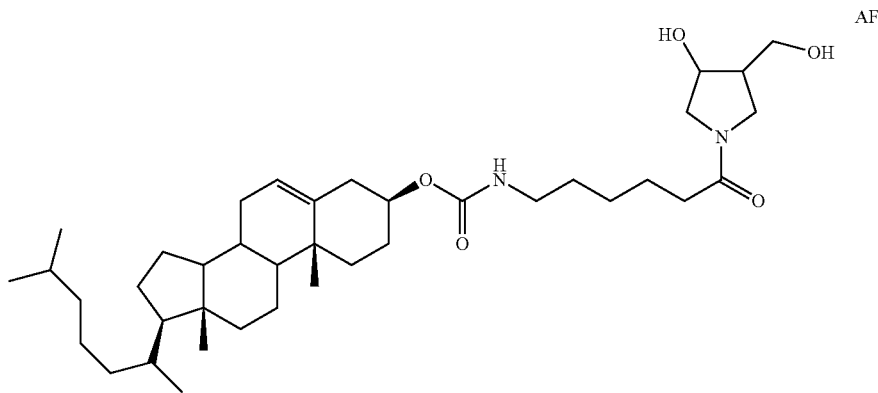 [SMILES: CC(C)CCCC(C)[C@H]1CCC2C3CC=C4C[C@@H](OC(=O)NCCCCCC(=O)N5CC(O)C(CO)C5)CC[C@]4(C)C3CC[C@@]21C]

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

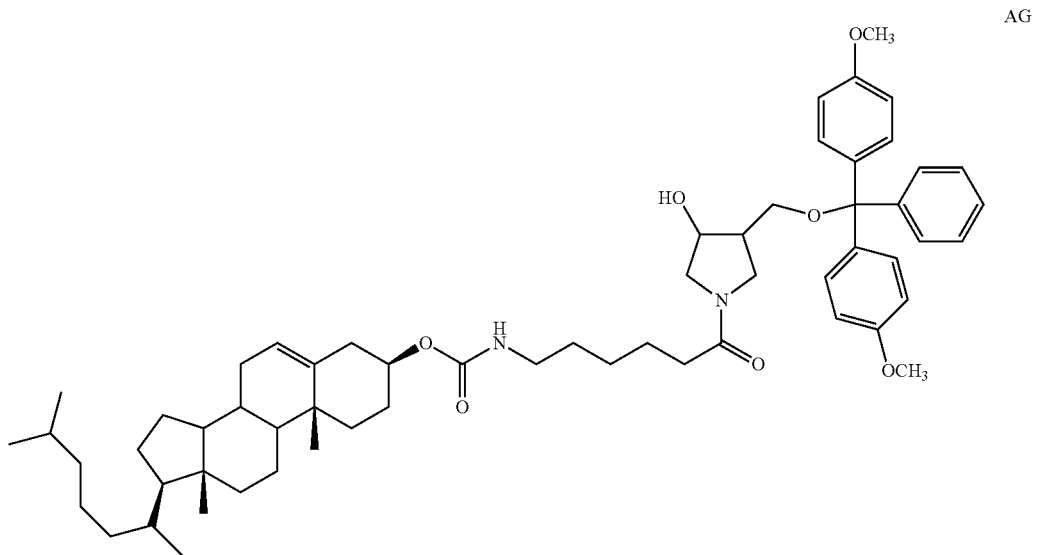 [SMILES: COc1ccc(C(OCC2CN(C(=O)CCCCCNC(=O)O[C@H]3CC[C@@]4(C)C(=CCC5C4CC[C@@]4(C)C5CC[C@@H]4C(C)CCCC(C)C)C3)CC2O)(c2ccccc2)c2ccc(OC)cc2)cc1]

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

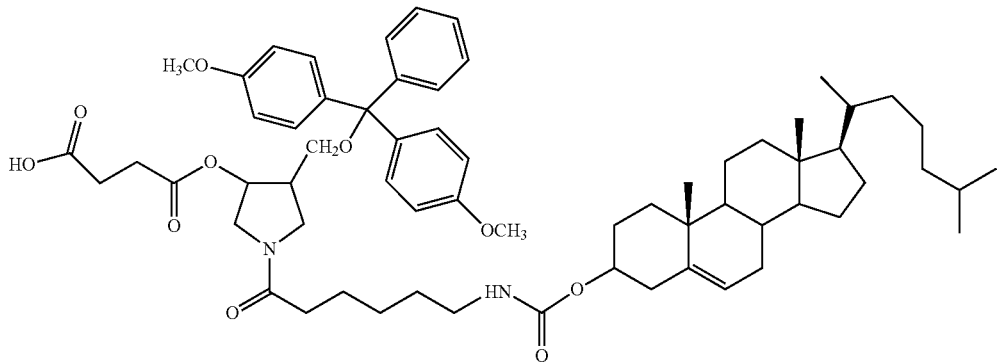

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG AI

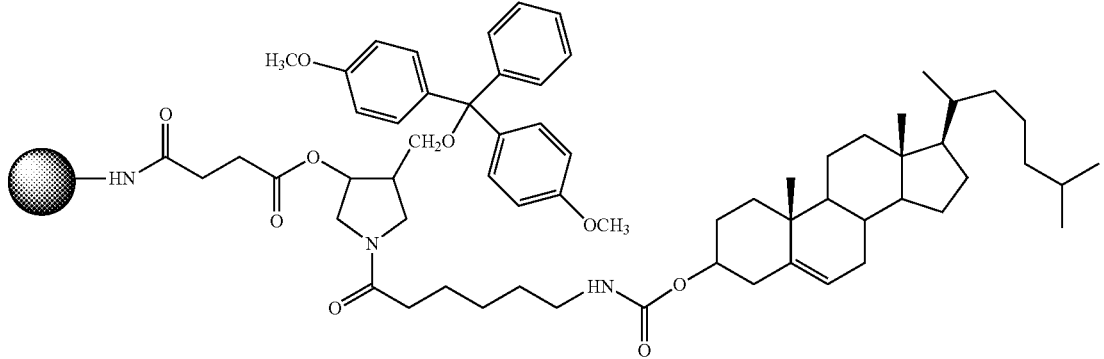

AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/ pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

Nucleic acid sequences are represented below using standard nomenclature, and specifically the abbreviations of Table 2.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A, a | 2'-deoxy-adenosine-5'-phosphate, adenosine-5'-phosphate |
| C, c | 2'-deoxy-cytidine-5'-phosphate, cytidine-5'-phosphate |
| G, g | 2'-deoxy-guanosine-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| N, n | any 2'-deoxy-nucleotide/nucleotide (G, A, C, or T, g, a, c or u) |
| Am | 2'-O-methyladenosine-5'-phosphate |
| Cm | 2'-O-methylcytidine-5'-phosphate |
| Gm | 2'-O-methylguanosine-5'-phosphate |
| Tm | 2'-O-methyl-thymidine-5'-phosphate |
| Um | 2'-O-methyluridine-5'-phosphate |
| Af | 2'-fluoro-2'-deoxy-adenosine-5'-phosphate |
| Cf | 2'-fluoro-2'-deoxy-cytidine-5'-phosphate |
| Gf | 2'-fluoro-2'-deoxy-guanosine-5'-phosphate |
| Tf | 2'-fluoro-2'-deoxy-thymidine-5'-phosphate |
| Uf | 2'-fluoro-2'-deoxy-uridine-5'-phosphate |
| A, C, G, T, U, a, c, g, t, u | underlined: nucleoside-5'-phosphorothioate |
| am, cm, gm, tm, um | underlined: 2-O-methyl-nucleoside-5'-phosphorothioate |

[a]capital letters represent 2'-deoxyribonucleotides (DNA), lower case letters represent ribonucleotides (RNA)

dsRNA Expression Vectors

In another aspect of the invention, Factor V Leiden mutant specific dsRNA molecules that modulate Factor V Leiden mutant gene expression activity are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are preferably DNA plasmids or viral vectors. dsRNA expressing viral vectors can be constructed based on, but not limited to, adeno-associated virus (for a review, see Muzyczka, et al., *Curr. Topics Micro. Immunol*. (1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natk. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980, 286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Preferably, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single Factor V Leiden mutant gene or multiple Factor V Leiden mutant genes over a period of a week or more are also contemplated by the invention. Successful introduction of the vectors of the invention into host cells can be monitored using various known meth auuccucgcc uguccagggt t                                                  21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 3
ccuggacagg cgaggaauat t                                                  21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 4
uauuccucgc cguccaggt t                                                   21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 5
cuggacaggc gaggaauact t                                                  21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic

```
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 6
guauuccucg ccuguccagt t                                                   21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 7
uggacaggcg aggaauacat t                                                   21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 8
uguauuccuc gccuguccat t                                                   21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
```

<223> OTHER INFORMATION: 2'-hydroxy corresponding base

<400> SEQUENCE: 9
ggacaggcga ggaauacagt t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 10
cuguauuccu cgccugucct t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 11
gacaggcgag gaauacagat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 12
ucuguauucc ucgccuguct t                                              21

<210> SEQ ID NO 13
<211> LENGTH: 21
<212> TYPE: DNA

<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 13
acaggcgagg aauacagagt t          21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 14
cucuguauuc cucgccugut t          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 15
caggcgagga auacagaggt t          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate

```
<220> FEATURE:
<221> NAME/KEY: modified_base
<222> LOCATION: (1)..(19)
<223> OTHER INFORMATION: 2'-hydroxy corresponding base

<400> SEQUENCE: 16
ccucuguauu ccucgccugt t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 17
aggcgaggaa uacagagggt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 18
cccucuguau uccucgccut t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 19
ggcgaggaau acagagggct t                                              21
```

-continued

```
<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 20
gcccucugua uccucgcct t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 21
gcgaggaaua cagagggcat t                                             21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 22
ugcccucugu auuccucgct t                                             21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 23
cgaggaauac agagggcagt t                                                  21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 24
cugcccucug uauuccucgt t                                                  21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 25
gaggaauaca gagggcagct t                                                  21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 26
```
gcugcccucu guauuccuct t                     21

```
<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 27
```
gcagaucccu ggacaggcat t                     21

```
<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 28
```
ugccugucca gggaucugct t                     21

```
<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 29
```
cagaucccug gacaggcaat t                     21

```
<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
```

```
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 30
uugccugucc agggaucugt t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 31
agaucccugg acaggcaagt t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 32
cuugccuguc cagggaucut t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base
```

```
<400> SEQUENCE: 33
gaucccugga caggcaaggt t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 34
ccuugccugu ccagggauct t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 35
aucccuggac aggcaaggat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 36
uccuugccug uccagggaut t                                              21

<210> SEQ ID NO 37
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 37
ucccuggaca ggcaaggaat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 38
uuccuugccu guccagggat t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 39
cccuggacag gcaaggaaut t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
```

```
<221> NAME/KEY: modified_base
<222> LOCATION: (1)..(19)
<223> OTHER INFORMATION: 2'-hydroxy corresponding base

<400> SEQUENCE: 40
auuccuugcc uguccagggt t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 41
ccuggacagg caaggaauat t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 42
uauuccuugc cuguccaggt t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 43
cuggacaggc aaggaauact t                                              21

<210> SEQ ID NO 44
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 44
guauuccuug ccuguccagt t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 45
uggacaggca aggaauacat t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 46
uguauuccuu gccuguccat t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
```

<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 47
ggacaggcaa ggaauacagt t                                            21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 48
cuguauuccu ugccugucct t                                            21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 49
gacaggcaag gaauacagat t                                            21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 50
ucuguauucc uugccuguct t                                            21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 51
acaggcaagg aauacagagt t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 52
cucuguauuc cuugccugut t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 53
caggcaagga auacagaggt t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:

```
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 54
ccucuguauu ccuugccugt t                                             21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 55
aggcaaggaa uacagagggt t                                             21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 56
cccucuguau uccuugccut t                                             21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base
```

```
<400> SEQUENCE: 57
ggcaaggaau acagagggct t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 58
gcccucugua uuccuugcct t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 59
gcaaggaaua cagagggcat t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 60
ugcccucugu auuccuugct t                                              21

<210> SEQ ID NO 61
<211> LENGTH: 21
<212> TYPE: DNA
<213> ORGANISM: Artificial Sequence
<220> FEATURE:
```

<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 61
caaggaauac agagggcagt t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 62
cugcccucug uauuccuugt t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 63
aaggaauaca gagggcagct t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 64
gcugcccucu guauuccuut t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 65
acaggcaagg aauacagagt t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 66
cucuguauuc cuugccugut t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 67
caggcaagga auacagaggt t                                              21

<210> SEQ ID NO 68
<211> LENGTH: 21

<212> TYPE: DNA
<213> ORGANISM: Artificial Sequence
<220> FEATURE:
<223> OTHER INFORMATION: Description of Artificial Sequence: Synthetic
    RNAi agent strand sequence
<220> FEATURE:
<223> OTHER INFORMATION: Description of Combined DNA/RNA Molecule:
    Synthetic RNAi agent strand sequence
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 68
ccucuguauu ccuugccugt t                                         21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
    RNAi agent strand sequence
<220> FEATURE:
<223> OTHER INFORMATION: Description of Combined DNA/RNA Molecule:
    Synthetic RNAi agent strand sequence
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 69
aggcaaggaa uacagagggt t                                         21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
    RNAi agent strand sequence
<220> FEATURE:
<223> OTHER INFORMATION: Description of Combined DNA/RNA Molecule:
    Synthetic RNAi agent strand sequence
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 70
cccucuguau uccuugccut t                                         21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
    RNAi agent strand sequence
<220> FEATURE:
<223> OTHER INFORMATION: Description of Combined DNA/RNA Molecule:
    Synthetic RNAi agent strand sequence
<220> FEATURE:
<223> OTHER INFORMATION: 5'-terminal nucleic acid is a nucleoside, i.e.

```
              base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 71
ggcaaggaau acagagggct t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 72
gcccucugua uuccuugcct t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 73
gcaaggaaua cagagggcat t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 74
ugcccucugu auuccuugct t                                              21
```

```
<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 75
caaggaauac agagggcagt t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      RNAi agent strand sequence
<220> FEATURE:
<223> OTHER INFORMATION: Description of Combined DNA/RNA Molecule:
      Synthetic RNAi agent strand sequence
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: (1)..(19)
<223> OTHER INFORMATION: 2'-hydroxy corresponding base

<400> SEQUENCE: 76
cugcccucug uauuccuugt t                                              21
```

We claim:

1. An isolated double-stranded ribonucleic acid (dsRNA) comprising a sense strand and an antisense strand and wherein the sense strand comprises at least 15 contiguous nucleotides of the nucleotide sequence of SEQ ID NO: 5 and the antisense strand comprises at least 15 contiguous nucleotides of the nucleotide sequence of SEQ ID NO: 6 respectively, wherein the dsRNA comprises a duplex structure at least 15 base pairs in length; and wherein the sense strand and the antisense strand are between 15 and 30 base pairs in length.

2. The dsRNA of claim 1, wherein the duplex structure is 19 base pairs in length.

3. The dsRNA of claim 1, wherein the sense strand consists of the nucleotide sequence of SEQ ID NO: 5 and the antisense strand consists of the nucleotide sequence of SEQ ID NO: 6, respectively.

4. The dsRNA of claim 1, wherein the dsRNA comprises at least one modified nucleotide.

5. The dsRNA of claim 4, wherein said modified nucleotide is chosen from the group of: a 2'-O-methyl modified nucleotide, a nucleotide comprising a 5'-phosphorothioate group, and a terminal nucleotide linked to a cholesteryl derivative or dodecanoic acid bisdecylamide group.

6. The dsRNA of claim 4, wherein said modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

7. An isolated cell comprising the dsRNA of claim 1.

8. The cell of claim 7, wherein the cell is a mammalian cell.

9. A pharmaceutical composition comprising the dsRNA of claim 1 and a pharmaceutically acceptable carrier.

10. A vector comprising a regulatory sequence operably linked to a nucleotide sequence that encodes at least one strand of the dsRNA of claim 1.

11. A cell comprising the vector of claim 10.

12. The cell of claim 11, wherein the cell is a mammalian cell.

13. A method for inhibiting the expression of a Factor V gene in a cell, the method comprising:
    (a) introducing into the cell the dsRNA of claim 1; and
    (b) maintaining the cell for a time sufficient to obtain degradation of the mRNA transcript of the Factor V gene, thereby inhibiting the expression of the Factor V gene in the cell.

14. The method of claim 13, wherein the cell is a mammalian cell.

* * * * *